US006451526B1

(12) United States Patent
Song et al.

(10) Patent No.: US 6,451,526 B1
(45) Date of Patent: Sep. 17, 2002

(54) SIMPLIFIED MUTATION DETECTION

(75) Inventors: Lu Song, Miami, FL (US); Dennis J. O'Kane, Rochester, MN (US); Kelly L. Krajnik, Rochester, MN (US); John A. Heit, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/232,273

(22) Filed: Jan. 15, 1999

Related U.S. Application Data (60) Provisional application No. 60/071,965, filed on Jan. 20, 1998, and provisional application No. 60/082,024, filed on Apr. 16, 1998.

(51) Int. Cl.$^7$ .............. C12Q 1/68; C12P 19/34; C07H 21/04; C07H 21/02; C07H 19/00

(52) U.S. Cl. .............. 435/6; 435/91.1; 435/91.2; 536/22.1; 536/23.1; 536/24.3; 536/24.31; 536/24.32; 536/24.33

(58) Field of Search .............. 435/6, 91.1, 91.2; 536/22.1, 24.3, 24.33

(56) References Cited

U.S. PATENT DOCUMENTS

| | | | |
|---|---|---|---|
| 4,683,195 A | | 7/1987 | Mullis et al. ............ 435/6 |
| 5,284,940 A | | 2/1994 | Lin et al. ............ 536/25.4 |
| 5,501,963 A | | 3/1996 | Burckhardt ............ 435/91.2 |
| 5,635,352 A | | 6/1997 | Urdea et al. ............ 435/6 |
| 5,807,675 A | * | 9/1998 | Davalian et al. ............ 435/6 |
| 6,013,439 A | * | 1/2000 | Lishanski et al. | |

FOREIGN PATENT DOCUMENTS

| | | | |
|---|---|---|---|
| WO | WO95/21938 | * | 8/1995 |
| WO | WO97/23646 | * | 7/1997 |

OTHER PUBLICATIONS

Amicosante M et al., Inactivation of Polymerase Inhibitors for *Mycobacterium tuberculosis* DNA Amplification in Sputum by Using Capture Resin, *J. Clinical Microbiology* 33(3):629–630 (1995).
Baker CS and Palumbi SR, Which Whales Are Hunted? A Molecular Genetic Approach to Monitoring Whaling, *Science* 265:1538–1539 (1994).
Babu PG et al., Letter to the Editor HTLV–1–Associated Myelopathy in South India, *AIDS Research and Human Retroviruses* 9(6):499–500 (1993).
Biswas I et al., Branch Migration Through DNA Sequence Heterology, *J. Mol. Biol.* 279:795–806 (1998).
Cambridge Healthtech Institute's Gene Mutational Analysis, Hyatt Regency Baltimore, Baltimore, Maryland, Sep. 30–Oct. 1, 1996.
Cripe LD et al., Structure of the gene for human coagulation Factor V, *Biochemistry*,31(15):3777–3785 (1992).
Ellis et al., MutS Binding Protects Heteroduplex DNA from Exonuclease Digestion In Vitro: A Simple Method for Detecting Mutations, *Nucleic Acids Research* 22(13):2710–2711 (1994).
Gwaltney SM and Oberst RD, Comparison of an Improved Polymerase Chain Reaction Protocol and the Indirect Hemagglutination Assay in the Detection of Eperythrozoon suis Infection, J. Vet. Diagn. Invest. 6:321–325 (1994).
Hunt DM et al., The Chemistry of John Dalton's Color Blindness, *Science* 267:984–988 (1995).
Hutchin T et al., A Molecular Basis for Human Hypersensitivity to Aminoglycoside Antibiotics, *Nucleic Acids Research* 21(18): 4174–4179 (1993).
Jenny RJ et al., Complete cDNA and Derived Amino Acid Sequence of Human Factor V, *Proc. Natl. Acad. Sci USA* 84:4846–4850 (1987).
Kane WH et al., Cloning of cDNAs Coding for the Heavy Chain Region and Connecting Region of Human Factor V, a Blood Coagulation Factor with Four Types of Internal Repeats, *Biochemistry* 26:6508–6514 (1987).
Levy L et al., Simple and Rapid Preparation of Infected Plant Tissue Extracts for PCR Amplification of Virus, Viroid, and MLO Nucleic Acids, *J. Virological Methods* 49:295–304 (1994).
Luck JE and Gillings MR, Rapid Identification of Benomyl Resistant Strains of *Botrytis cinerea* Using the Polymerase Chain Reaction, *Mycol. Res.* 99(12):1483–1488 (1995).
Nerurkar V et al., Sequence Analysis of Human T Cell Lymphotropic Virus Type I Strains from Southern India: Gene Amplification and Direct Sequencing from Whole Blood Blotted onto Filter Paper, *J. General Virology* 74:2799–2805 (1993).
Nerurkar V et al., HIV Type 1 Subtype E in Commercial Sex Workers and Injection Drug Users in Southern Vietnam, *AIDS Research and Human Retroviruses* 12(9):841–843 (1996).
Panyutin IG and Hsieh P, Formation of a Single Base Mismatch Impedes Spontaneous DNA Branch Migration, *J. Mol. Biol.* 230:413–424 (1993).

(List continued on next page.)

Primary Examiner—Jeffrey Siew
(74) Attorney, Agent, or Firm—Fish & Richardson P.C., P.A.

(57) ABSTRACT

The invention involves methods and materials for detecting a mutation in the genome of an organism. Specifically, the invention provides compositions of oligonucleotides and diagnostic kits that can be used to amplify nucleic acid sequences such that if heterologous amplified fragments are present, then stable nucleic acid branching structures are formed and detected from a cell lysate mixture containing the amplified nucleic acid. The formation of stable nucleic acid branching structures is particularly useful for providing a mechanism to detect heterologous alleles verses homozygous alleles since homozygous amplified products do not form stable nucleic acid branching structures. In addition, the invention provides methods of detecting heterologous Factor V alleles as well as homozygous wild-type and homozygous mutant Factor V alleles.

16 Claims, 3 Drawing Sheets

OTHER PUBLICATIONS

Parsons BL and Heflich RH, Evaluation of MutS as a Tool for Direct Measurement of Point Mutations in Genomic DNA, *Mutation Research* 374:277–285 (1997).

Schizas NV et al., An Efficient DNA Extraction Method for Small Metazoans, *Molecular Marine Biology and Biotechnology* 6(4):381–383 (1997).

Stone GG et al., Detection of *Salmonella typhimurium* from Rectal Swabs of Experimentally Infected Beagles by Short Cultivation and PCR–Hybridization, *J. Clinical Microbiology* 33(5):1292–1295 (1995).

Stone GG et al., Detection of Salmonella Serovars from Clinical Samples by Enrichment Broth Cultivation–PCR Procedure, *J. Clinical Microbiology* 32(7):1742–1749 (1994).

* cited by examiner

FIG. 2 CRUCIFORM STRUCTURE TAGGING

FIG. 3
CRUCIFORM STRUCTURE DETECTION

SIMPLIFIED MUTATION DETECTION

RELATED APPLICATION

This application claims priority under U.S. provisional application Ser. No. 60/071,965, filed Jan. 20, 1998 and U.S. provisional application Ser. No. 60/082,024, filed Apr. 16, 1998.

BACKGROUND

1. Technical Field

The invention relates to methods and materials involved in the rapid detection of mutations.

2. Background Information

Many mutations in human genes exist and are associated with disease or disease risk. For example, a single mutation in exon 10 of the cystic fibrosis gene, delta F508, is associated with cystic fibrosis. In addition, a point mutation in Factor V appears to be associated with thrombosis. Briefly, Factor V is a polypeptide involved in the coagulation cascade. Normally, activated protein C deactivates Factor V to regulate the cascade of coagulation events. One particular mutant form of Factor V, known as Factor V Leiden, contains a single point mutation (G1691A) that renders the polypeptide resistant to activated protein C. Interestingly, Factor V Leiden is found in almost every ethnic group. For example, about 5–7% of the individuals of European or Scandinavian ancestry are carriers. In addition, about 1–2% of the population of other ancestries are carriers. Rather strikingly, over 20% of patients with thrombosis are carriers. Thus, the mutation found in Factor V Leiden may be involved in blood disorders.

Current methods used to detect mutations such as Factor V Leiden (e.g., bidirectional PCR amplification of specific alleles (bi-PASA), or restriction fragment length polymorphism (RFLP)), rely on allele specific primers to amplify DNA that is then analyzed by gel electrophoresis to detect the presence or absence of a specific fragment. The use of gel electrophoresis as a method of detection greatly increases the time required to analyze a sample and limits the number of samples that can be analyzed. Thus, any method that rapidly and accurately detects mutations and does not require gel electrophoresis would be desirable.

SUMMARY

The invention involves methods and materials for detecting mutations. Specifically, the invention is based on the discovery of a rapid and reliable detection assay that does not require nucleic acid purification or extraction. The elimination of the need to purify nucleic acid greatly reduces the time needed to perform an assay and does not compromise accuracy. In addition, this simplification of the detection assay reduces the number of steps required for sample preparation and thus reduces the chances of operator error and contamination as well as exposure of the operator to potentially infectious material. Diagnostic kits containing the ingredients needed to perform this simplified mutation detection assay are provided by the invention. Such kits are particularly useful to diagnostic laboratory personnel since the kits can provide all the necessary ingredients in a more uniform manner than otherwise would be available. For example, samples can be analyzed at separate facilities and the results accurately compared to each other since the ingredients in each kit can be prepared in a similar manner by a common vendor. This is particularly important for buffer solutions, oligonucleotide primers, and detection reagents. The invention also provides specific oligonucleotide primers and nucleic acid amplification conditions that allow heterologous amplification products of the human Factor V gene to form stable branching structures. The formation of these stable branching structures is particularly useful for providing a mechanism to detect heterologous alleles verses homozygous alleles. In addition, the invention provides oligonucleotide primers as well as assay conditions that allow for the rapid and accurate screening of multiple samples.

In general, the invention features a composition containing oligonucleotides. The composition amplifies a region of Factor V genomic sequence during a nucleic acid amplification reaction such that amplified products that are heterologous form stable branching structures. In addition, the region contains a potential mutation site. The composition can contain two oligonucleotides that are identical in nucleic acid sequence (e.g., SEQ ID NO:1). Each of the two oligonucleotides can have a different label attached at the 5' end (e.g., biotin and digoxigenin). Further, the composition can contain two oligonucleotides each having a 5' portion and a 3' portion. The 5' portions of the two oligonucleotides are different in nucleic acid sequence, and the 3' portions of the two oligonucleotides are identical in nucleic acid sequence. The 3' portions hybridize to a sequence flanking the mutation site during the nucleic acid amplification reaction. One of the two oligonucleotides can have a nucleic acid sequence as set forth in SEQ ID NO:2, 3, 4, 5, 6, or 7. The amplified products can be less than about 300 bases in length in which case one of the oligonucleotides can have a nucleic acid sequence as set forth in SEQ ID NO:4, 5, 6, or 7. Alternatively, the oligonucleotides of the composition can produce false positive results in a LOCI mutation detection assay less frequently than when Dig-Primer1, Bt-Primer1, Primer2, and Primer3 primers are used in the LOCI mutation detection assay. In this case, the oligonucleotides can include Dig-Primer1, Bt-Primer1, Primer4, and Primer5.

Another aspect of the invention features an oligonucleotide that consists of the sequence as set forth in SEQ ID NO:1, 2, 3, 4, 5, 6, 7, 8, 9, 10, 11, 12, 13, or 14.

In another aspect, the invention features a method of detecting heterologous Factor V alleles in an organism. The method includes amplifying a region of Factor V nucleic acid from the organism using oligonucleotides such that amplified products that are heterologous form stable branching structures, and detecting the presence or absence of the stable branching structures. The region contains a potential mutation site and the presence of the stable branching structures is indicative of the presence of the heterologous Factor V alleles in the organism. LOCI can be used for the detecting step. Alternatively, a sandwich immunoassay can be used for the detecting step.

Another embodiment of the invention features a method of detecting homozygous mutant Factor V alleles in an organism. The method includes amplifying a region of Factor V nucleic acid from the organism using oligonucleotides to form amplification products; contacting the amplification products with a solution to form a mixture; and detecting the presence or absence of stable branching structures in the mixture. The region contains a potential mutation site and the solution contains homozygous wild-type Factor V products amplified using the oligonucleotides. The stable branching structures are formed between the amplification products and the homozygous wild-type Factor V products. In addition, the presence of the stable branching structures is indicative of the presence of the homozygous mutant Factor V alleles in the organism. LOCI can be used for the detecting step. Alternatively, a sandwich immunoassay can be used for the detecting step.

Another aspect of the invention features a diagnostic kit for nucleic acid extraction-free detection of heterologous alleles in an organism (e.g., human). The kit contains a cell lysis reagent and two oligonucleotides. The two oligonucleotides are identical in nucleic acid sequence (e.g., SEQ ID NO:1) with each of the two oligonucleotides having a different label attached at the 5' end (e.g., biotin and digoxigenin). In addition, the two oligonucleotides hybridize to a first region of genomic sequence during a nucleic acid amplification reaction and the first region flanks a potential mutation site. The cell lysis reagent can contain an ingredient that inactivates a polymerase inhibitor. The genomic sequence can contain a Factor V genomic sequence. Alternatively, the genomic sequence can contain a cystic fibrosis genomic sequence. Further, the kit can contain two additional oligonucleotides each having a 3' portion and a 5' portion. The 5' portions are different in nucleic acid sequence, and the 3' portions are identical in nucleic acid sequence. The 3' portions hybridize to a second region of the genomic sequence during the nucleic acid amplification reaction, and the second region is located on a side of the potential mutation site that is opposite the side of the first region. The second region can be downstream or upstream of the potential mutation site. One of the two additional oligonucleotides can have a sequence as set forth in SEQ ID NO:2, 3, 4, 5, 6, or 7.

Another aspect of the invention features a method of comparing nucleic acid sequences of alleles in an organism. The method includes amplifying a nucleic acid region of the alleles in a cell lysate to form a cell lysate mixture having amplification products; analyzing the cell lysate mixture for the presence or absence of stable nucleic acid branching structures; and classifying the alleles as heterologous if the stable nucleic acid branching structures are present in the cell lysate mixture.

In another embodiment, the invention features a method of detecting homozygous mutant alleles in an organism. The method includes amplifying a nucleic acid region of the alleles in a cell lysate using oligonucleotides to form a cell lysate mixture having amplification products; contacting the cell lysate mixture with a solution to form a second mixture; analyzing the second mixture for the presence or absence of stable nucleic acid branching structures; and classifying the alleles as homozygous mutant alleles if the stable nucleic acid branching structures are present in the second mixture. The solution contains homozygous wild-type products amplified from homozygous wild-type alleles using the oligonucleotides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides methods and materials related to the detection of a mutation in a genome of an organism. Specifically, the invention provides a simplified method for detecting mutations as well as diagnostic kits containing the ingredients needed to perform a simplified mutation detection assay. In addition, the invention provides oligonucleotide primers as well as assay conditions that allow for rapid and accurate detection of Factor V Leiden and a mutation in the cystic fibrosis gene.

In general, the simplified mutation detection method provided by the invention involves the detection of heterologous alleles (i.e., alleles differing in sequence) from a nucleic acid amplification reaction mixture prepared directly from a cellular sample (e.g., a cell lysate). Thus, the method does not involve the purification of nucleic acid. The term "cell lysate" as used herein refers to any solution that contains the cellular constituents (e.g., proteins, lipids, carbohydrates, and nucleic acid) produced upon disruption of a cell. For example, nucleic acid isolated from a solution of disrupted cells is not a cell lysate. Cell lysate solutions, however, can include, without limitation, a solution of lysed cells that is treated such that selected molecules are removed or rendered inactive. It follows that this solution remains substantially "crude" with respect to most purified cellular constituents. For example, a cell lysate can be a solution of lysed cells that is treated with an agent that inactivates or removes polymerase inhibitors (U.S. Pat. No. 5,284,940). In addition, a cell lysate can be a solution of lysed cells that is treated with an anti-coagulant (U.S. Pat. No. 5,501,963).

Any method can be used to lyse cells in a cellular sample. For example, osmotic shock, sonication, heating, physical disruption, microwave treatment, and alkaline lysis are methods that can be used to lyse cells. In addition, the GeneReleaser™ kit (BioVentures, Inc) can be used to produce a cell lysate. A cellular sample can be any type of cellular sample including, without limitation, blood samples, urine sedimentary cell samples, throat swabs, and skin samples. For example, a cellular sample such as whole blood can be collected from a human, lysed, and the nucleic acid region of interest amplified by a nucleic acid amplification reaction. A nucleic acid amplification reaction can be any reaction provided the desired nucleic acid region is amplified. For example, a PCR reaction can be performed using Taq polymerase.

In general, PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a region of nucleic acid can be amplified from RNA or DNA. For example, a region of nucleic acid can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Figure 1:
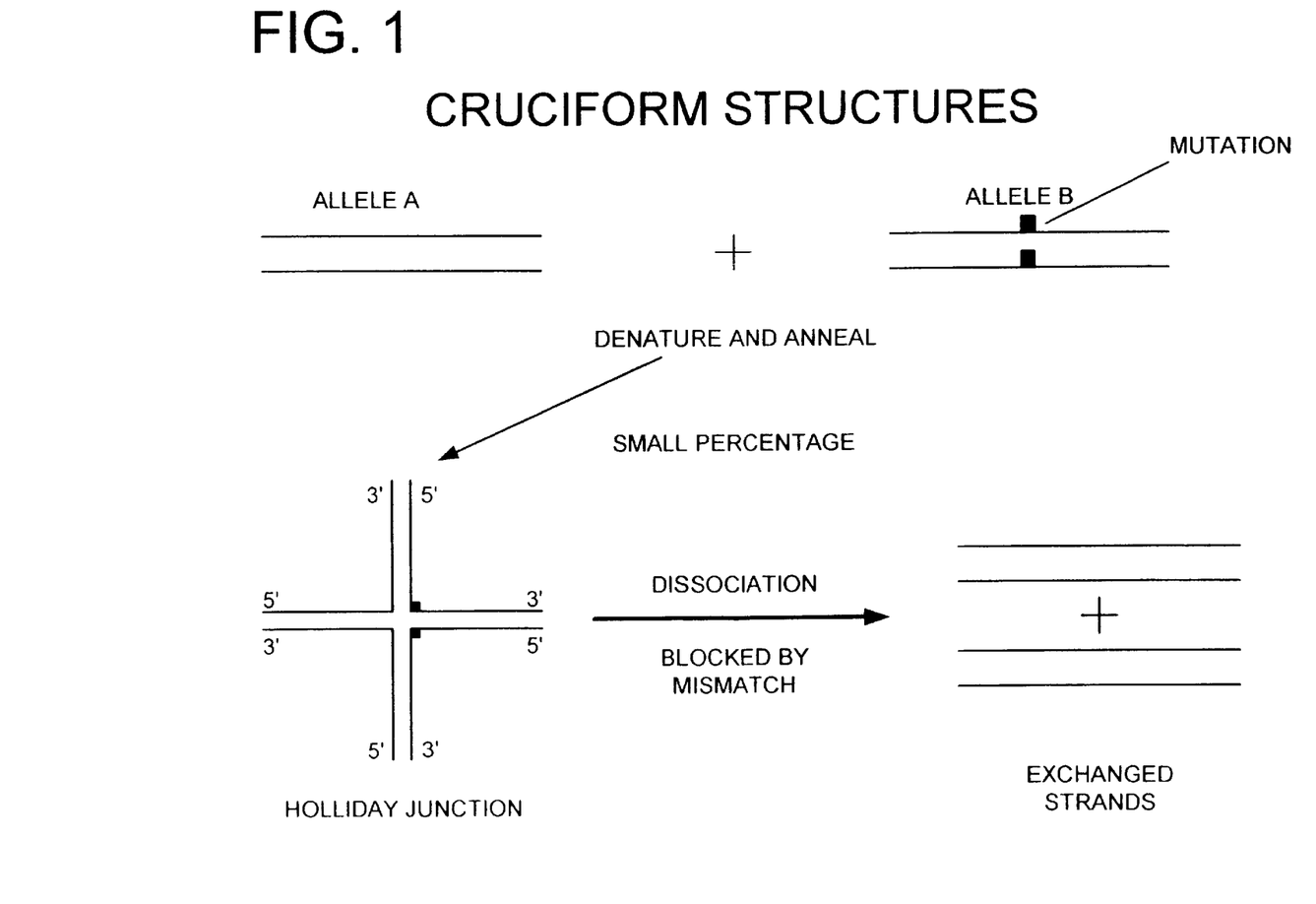
FIG. 1 is a diagram depicting the nucleic acid branching structure that is stabilized when formed from heterologous alleles.

The products resulting from a nucleic acid amplification reaction are collectively referred to as amplification products or amplified products. Such products can be subjected to conditions that promote the formation of stable branching structures. For example, amplification products can be incubated at about 96° C. for about 2 minutes to melt any double stranded nucleic acid, and then can be incubated at about 65° C. for about 30 minutes to initiate stable branching structure formation after which the products can be maintained at 4° C. until analyzed. For the purpose of this invention, a stable branching structure refers to a Holliday Junction or cruciform structure of nucleic acid whose dissociation is blocked by at least one mismatch within the amplified region of nucleic acid (FIG. 1). Thus, the amplification of a region of nucleic acid from homologous alleles would not result in stable branching structures since the amplified region of nucleic acid does not contain a mismatch that can prevent dissociation. On the other hand, the amplification of a region of nucleic acid from heterologous alleles would result in stable branching structures since the amplified region of nucleic acid contains a mismatch that can prevent dissociation.

Figure 2:
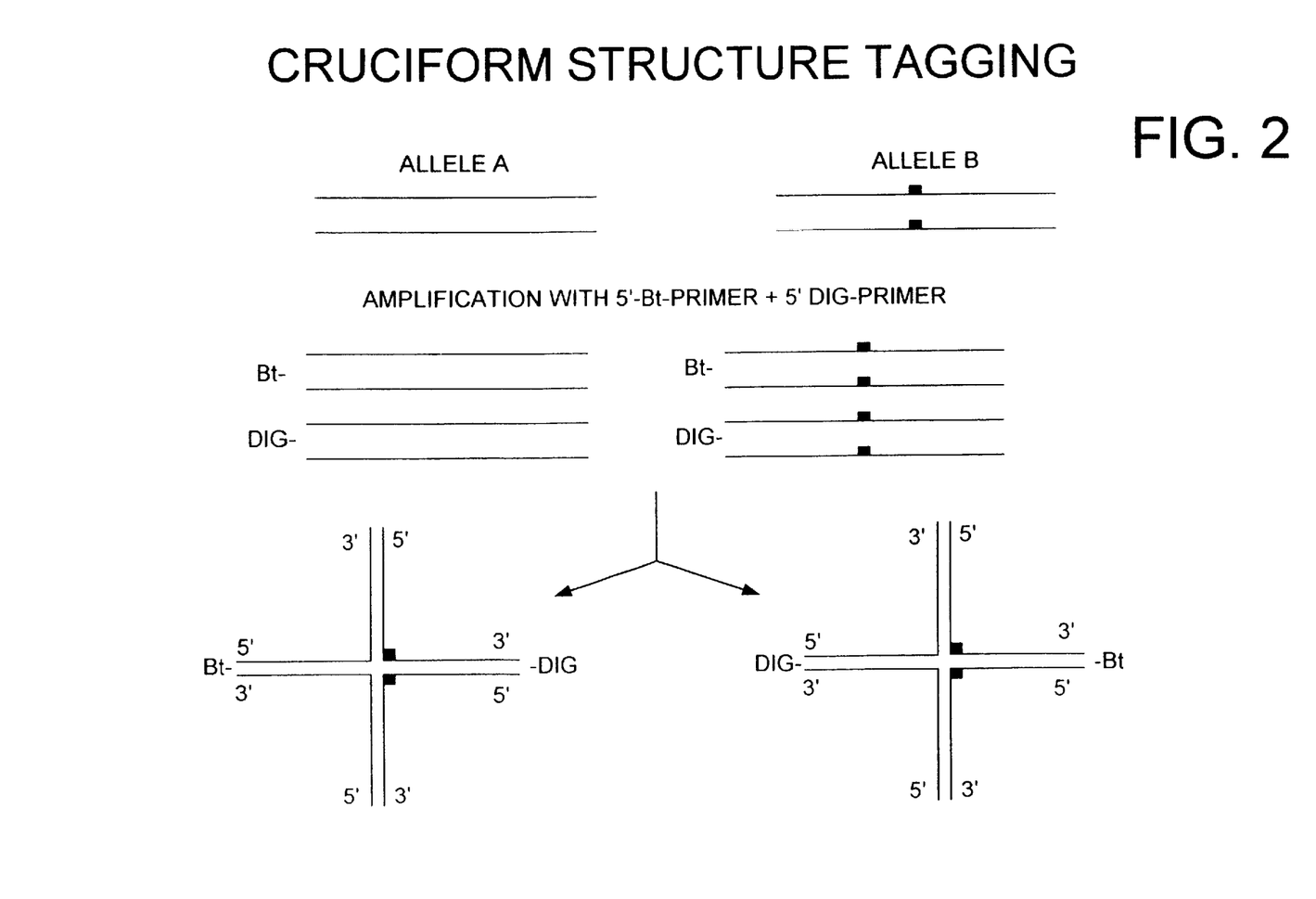
FIG. 2 is a diagram depicting the nucleic acid branching structure formed from heterologous alleles using primers that are tagged with either biotin (Bt) or digoxigenin (Dig).

In general, a nucleic acid amplification reaction that is used to generate stable branching structures contains four oligonucleotide primers. Two of the four oligonucleotide primers hybridize, during the nucleic acid amplification reaction, to a genomic sequence upstream of a potential mutation site. These two primers have identical sequences but different 5' labels. Examples of 5' labels include, without limitation, binding agents such as antigens and ligands. For example, an antigen such as digoxigenin and a ligand such as biotin can be used as 5' labels (FIG. 2).

The other two oligonucleotide primers have identical 3' portions and different 5' portions. The identical 3' portions of each primer can hybridize, during the nucleic acid amplification reaction, to any genomic sequence downstream of a potential mutation site. The different 5' portions of each primer can have a sequence such that this portion does not hybridize to any of the genomic sequences flanking the potential mutation site. Thus, the two upstream primers can have different 5' labels and the two downstream primers can have different 5' sequences. It is noted that these primers can be switched such that the two upstream primers have different 5' sequences and the two downstream primers have different 5' labels.

A potential mutation site is any nucleic acid position that is found or suspected to have a particular base in one organism that is different from the particular base found at that same position in another organism of the same species. Thus, any polymorphism is considered a potential mutation site. As described herein, any region of the human genome can be a region of nucleic acid containing a potential mutation site. For example, the region can be from genes associated with disease such as β-APP, ApoE4, cystic fibrosis, Factor V, and HFE (hemochromotosis) genes as well as oncogenes such as the RET proto-oncogene. Other examples of genes that can be analyzed are listed in Tables I and II.

TABLE I

Gene associated with venous thrombosis and cardiovascular disease

| Gene | #Mutations | Prevalence (VT) |
|---|---|---|
| Venous Thrombosis | | |
| Factor V Leiden | 2 (1 rare) | 45% (European) |
| Prothrombin Elevated | 1 | 18% (European) |
| Dysfibrinoginemia | >11 | 1% |
| Protein S Deficiency | >69 | 5.7% |
| Antithrombin Deficiency | >79 | 4.3% |
| Protein C Deficiency | >160 | 5.7% |
| Unknown | ????? | ~20% |

| Gene | #Mutations |
|---|---|
| Cardiovascular Disease | |
| apoA | 21 |
| apoA-4 | 4 |
| apoB | 17 |
| apoC | 11 |
| apoE | 29 |
| LP(a) | 2 |
| Hyperlipoproteinemia (Lipoprotein Lipase) | 35 |
| Hypercholesterolemia (LDL Receptor) | 54 |

TABLE II

Addition gene associated with disease

| Condition | Gene | Mutations | Prevalence | Comments |
|---|---|---|---|---|
| Hemo-chromatosis | HLA-H | 1 | 1/14 Heterozygous 1/250 Homozygous | Therapy available |
| Hyperhomo-cysteinuria | MTHFR | 7 | | Therapy available |
| Hyperhomo-cysteinemia | MTHFR | 1 | 9–17% Homozygous 31–39% Heterozygous | Therapy available |
| Hyperhomo-cysteinemia | Cystathionine-β-synthase | 3 | | Therapy available |
| Medium Chain Fatty Acid Coenzyme A Reductase | | >9 | 1 ~ 90% | Therapy available Possible new-born screening |
| Pancreatic Cancer | k-RAS | 1 | ~20,000 new cases annually | Screen: new diabetics, pancreatitis, select other cancer syndromes |
| Multiple Endocrine Neoplasia Type II/Familial Medullary Thyroid Cancer | RET proto-oncogene | 28 | | |
| Cancer | p53 | numerous | 25–50% of cancers | |

Figure 3:
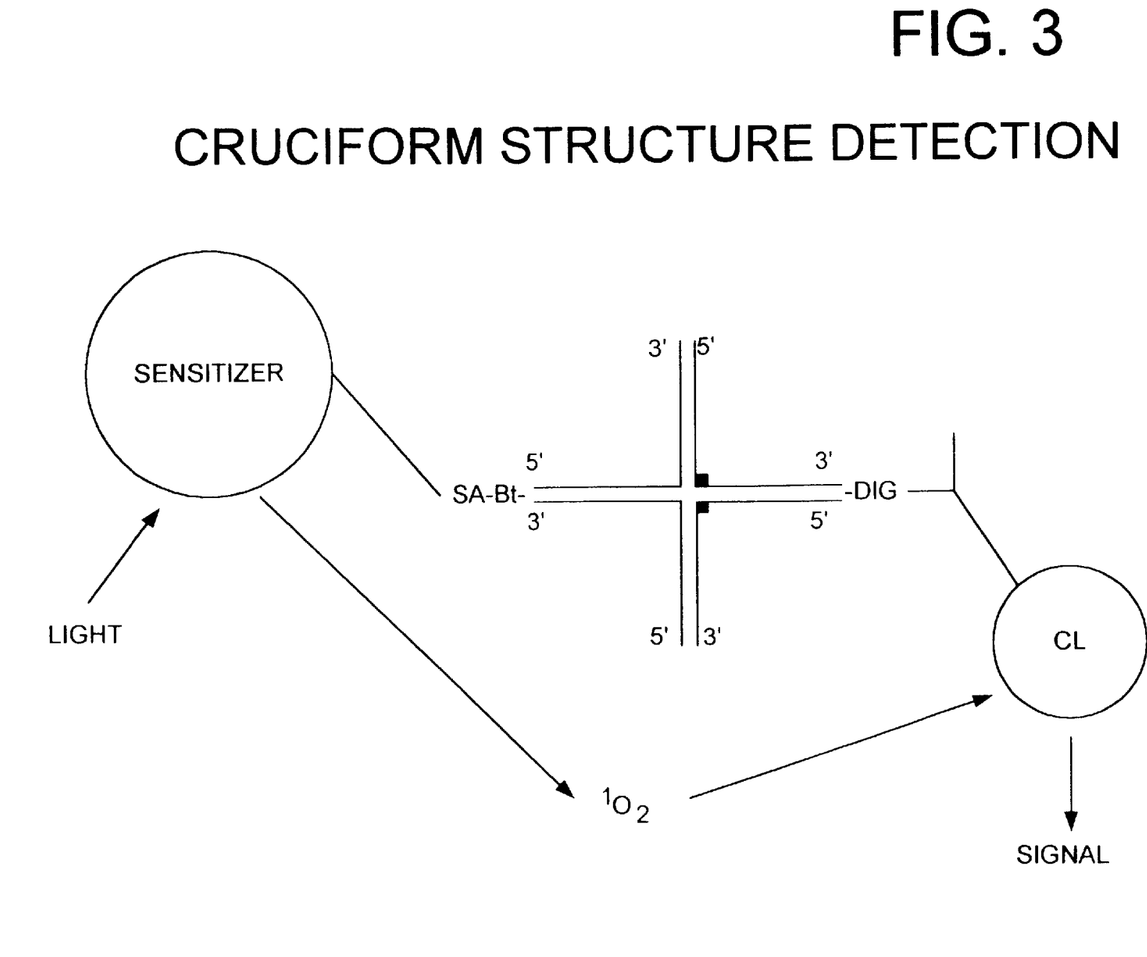
FIG. 3 is a diagram depicting a process of detecting stabilized branching structures.

Several different methods can be used to detect the presence or absence of stable branching structures when nucleic acid is amplified from purified DNA or a cell lysate. Again, the presence of stable branching structures indicates that the amplified region was generated from heterologous alleles that were used as templates during the amplification reaction. In general, the invention provides detection methods that involve fluid phase detection assays and not gel electrophoresis. For example, luminescence oxygen channeling immunoassays (LOCI) can be used to detect the presence or absence of stable nucleic acid branching structures from a cell lysate mixture containing amplified nucleic acid (FIG. 3). In addition, sandwich immunoassays can be used to detect the presence or absence of stable nucleic acid branching structures.

It is noted that the presence of heterologous alleles can be detected from the cell lysate mixtures described herein. For example, denaturing reverse-phase high-performance liquid chromatography (D-HPLC) can be used to discriminate between homo- and hetero- duplex nucleic acid within such mixtures, while MutS-based assays can be used to detect heteroduplex nucleic acid within such mixtures. Briefly, MutS-based assays use a bacterial polypeptide (MutS) that specifically binds the mis-match site of heteroduplex nucleic acid (Parsons and Heflich, *Mutat Res* 374(2):277–85 (1997) and Ellis et al., *Nucleic Acids Res* 22(13):2710–11 (1994)).

Using a stable nucleic acid branching structure assay, a Factor V Leiden analysis can proceed as follows. A fragment containing the point of mutation in Factor V is specifically amplified using PCR. Under certain conditions, the amplified DNA of a heterozygous carrier (i.e., an individual having heterologous Factor V alleles) forms a stable nucleic acid branching structure that brings a donor/acceptor together such that a chemiluminescence signal is generated (FIGS. 1–3). A positive chemiluminescence signal is observed first in a heterozygous specimen. Amplified DNA from an individual having homozygous wild-type Factor V, or homozygous Factor V Leiden alleles, results in a negative signal. If fragments from an individual homozygous for Factor V Leiden, however, are mixed with fragments from a known wild-type Factor V sample, then an artificial heterozygous DNA sample will be generated from an original homozygous specimen. Therefore, a homozygous Factor V Leiden carrier is detected by the mixing test incorporated as part of this assay. The presence of stable branching structures can be detected using a LOCI format or a microtitre plate format. In both cases, streptavidin and anti-digoxigenin can be used to identify the presence of stable branching structures containing both biotin and digoxigenin.

A region of genomic Factor V nucleic acid containing two potential mutation sites is as follows: ttatttattatcat-gaaataactttgcaaatgaaaacaattttgaatatattttctttcaG GCAGGAACAACACCATG-ATCAGAGCAGTTCAACCAGGGGAAAC-CTATACTTATAAGTGGAACATCTTAGAGTTT GAT-GAACCCACAGAAAATGATGCCCAGTGCTTAACAA GACCATACTACAGTGACGT GGACATCATGARAGA-CATCGCCTCTGGGCTAATAGGACTACT-TCTAATCTGTAAGAG CAGATCCCTGGACAG-GCRAGGAATACAGgtattttgtccttgaagtaacctttcagaaattctg agaatttcttctgg ctagaacatgttaggtctcctg-gctaaataatggggcatccttcaa-gagaacagtaattgtcaagtagtcctttttagcaccagtgtgataaca tttat-tcttttttttttttgtct (SEQ ID NO: 15). The first stretch of lower case bases represents sequences from intron 9, while the second stretch of lower case bases represents sequence from intron 10. The capitalized bases are sequences from exon 10 with the first bold R being position 1628 and the second bold R being position 1691 (the Factor V Leiden position). An R indicates either a G or A, while the wild-type Factor V would have a G at both of these positions.

The invention will be further described in the following examples, which do not limit the scope of the invention described in the claims.

EXAMPLES

Example 1—Factor V Leiden Detection from Purified DNA

This protocol combined with the selection of the primers selectively amplifies the region of the Factor V Leiden mutation, and eliminates non-specific binding as well as the amplification of genes having homology to Factor V, such as Factor VIII. In addition, the stable nucleic acid branching structures formed between heterozygous strands of DNA generated by this protocol were detected by a LOCI method without having to run electrophoresis gels.

Four primers were designed. The two upper primers target the 5'-end of the exon 10 of the Factor V gene. Each of these two primers was designed to have the same sequence (5'-CAGGCAGGAACAACACCATGAT-3'; SEQ ID NO:1) with a different binding agent attached at the 5'-end: one having digoxigenin (Dig-Primer1) and the other having biotin (Bt-Primer1). Both Dig-Primer1 and Bt-Primer1 were obtained from OLIGOSETC (Wilsonville, Oreg.) in a purified and lyophilized form. Before use, each primer was dissolved in distilled water to form a stock solution having a concentration of 25 $\mu$M. The stock solutions of these primers were stored at −20° C.

The two lower primers (Primer2 and Primer3) also target exon 10 of the Factor V gene. These two primers were designed to have an identical sequence at the 3'-end and a different sequence at the at the 5'-end of the primer. The sequence of Primer2 (SEQ ID NO:2) and Primer3 (SEQ ID NO:3) is as follows with the identical sequences being underlined:
5'-ACCATGCTCGAGATTACGAGTTATCACACTGGT GCTAAAAAGGA-3' (SEQ ID NO:2)
5'-GATCCTAGGCCTCACGTATTTTATCACACTGGT GCTAAAAAGGA-3' (SEQ ID NO:3)

Both lower primers (Primer2 and Primer3) were synthesized by the CORE Facility at Mayo Foundation. Briefly, the primers were desalted using a Pharmacia NAP-25 column and eluted from the column with distilled water in 1 mL fractions. The absorption at 260 nm ($A_{260}$) of each fraction was measured using an HP8452A Diode Array Spectrophotometer and a quartz micro cell (HP QS 0.200) that has a light path of 0.200 cm. Fractions with significant $A_{260}$ of each primer were pooled and concentrated using a Speed-Vac. The $A_{260}$ was measured and the final concentration C ($\mu$g/mL) of each primer was calculated using the formula: C=5×33×$A_{260}$ $\mu$g/mL. The molar concentration (CM) can be calculated using $C_M$=C×1000/(325×N) $\mu$M, where N is the number of bases in the primer. Stock solutions of these primers were stored at −20° C.

In general, the following methods involved four steps: (1) purification of nucleic acid from a cellular sample, (2) amplification of target DNA by PCR, (3) formation of branched DNA between strands of heterozygous alleles, and (4) detection of the branched DNA using the luminescence oxygen channeling immunoassay (LOCI). These steps were used to detect a heterozygous carrier while a mixing test was done to detect a homozygous carrier.

Standard nucleic acid isolation techniques (AGTC Kit®; Analytic Genetics Testing Center) were used to isolate genomic DNA from white blood cells. For each patient, genomic DNA was precipitated by ethyl alcohol and re-dissolved in TE buffer (10 mM Tris, 1 mM EDTA, pH 8.0). The concentration of genomic DNA from each patient varied, but was generally around 50 mg/$\mu$L. It was not necessary to adjust each genomic DNA to an exact concentration as long as it was around 50 ng/$\mu$L.

Once the genomic DNA was isolated, the target DNA was amplified using a GeneAmp PCR System 2400 (Perkin Elmer) PCR machine. To prevent PCR carry-over and contamination, the PCR reagents and DNA templates (especially DNA amplicon) were physically separated in two different rooms. The PCR reagents included nuclease-free water (PT#P119C; Promega), PCR tubes (MicroAmp Reaction Tubes; Perkin Elmer), 10X polymerase buffer, 10 mM dNTP mix (BRL), 50 mM $MgCl_2$, a set of micropipets, and pipette tips. The 10X polymerase buffer was supplied by Stratagene with the native Pfu DNA polymerase and contained 200 mM Tris-HCI (pH 8.0); 20 mM $MgCl_2$; 100 mM KCl; 60 mM $(NH4)2SO4$; 1% Triton X-100; and 100 µg/ml nuclease-free BSA. The 50mM $MgCl_2$ was either obtained from BRL or made in large quantities to maintain a consistent concentration. In addition, the 10X polymerase buffer, 10 mM dNTP mix (BRL), and 50 mM $MgCl_2$ were stored in at −20° C.

Two different forms of the proofreading DNA polymerase *Pyrococcus furiosus* (Pfu polymerase) were used: native and cloned. Both were obtained from Stratagene and had a concentration of 2.5 U/µL. The native Pfu polymerase can give the best signal-to-noise ratio, although constant supply can be a problem. In addition, two different protocols were developed, one for use with the native Pfu polymerase and another for use with the cloned Pfu polymerase.

The following methods and materials were used in conjunction with the native Pfu polymerase. Fifteen minutes before use, the 10X polymerase buffer, 10 mM dNTP mix, 50 mM $MgCl_2$, and a primer mix was warmed to room temperature. The primer mix was made as follows. A 100 µL solution of each primer (Dig-Primer1; Bt-Primer1; Primer2; and Primer3) was made in double distilled water to have a concentration of 12.5 µM. An equal volume of each 100 µL solution then was mixed together to make the primer mix. The final concentration of each primer in this primer mix was 3.125 µM.

The PCR reaction buffer (L-Buffer), polymerase working solution (U-Buffer), and DNA dilution buffer (G-Buffer) were made in separated 250-µL Eppendorf tubes. For 10 PCR reactions each having a total volume of 50 µL, the L-Buffer, U-Buffer, and G-Buffer was made as follows:

|  | L-Buffer | U-Buffer | G-Buffer |
| --- | --- | --- | --- |
| Nuclease-free water | 61.25 µL | 103.75 µL | 207.5 µL |
| 10 X polymerase buffer | 12.5 µL | 12.5 µL | 25 µL |
| 50 mM $MgCl_2$ | 8.75 µL | 8.75 µL | 17.5 µL |
| Primer mix | 40 µL |  |  |
| 10 mM dNTP mix | 5 µL |  |  |
| Native Pfu polymerase |  | 6 µL |  |
| Total volume | 127.5 µL | 131 µL | 250 µL |

Once the ingredients were added, the tubes were mixed gently by mid-speed vortex.

To setup each PCR reaction, 12.5 µL of L-Buffer was transferred to each labeled PCR tube and 25 µL of G-Buffer was transferred to each labeled DNA tube (250-µL Eppendorf tube). The U-Buffer was maintained on ice and the labeled PCR and DNA tubes as well as the U-Buffer were brought to the PCR room where 1 µL of genomic DNA was added to each labeled DNA tube. The labeled DNA tubes then were vortexed and the contents transferred to each labeled PCR tube. One positive control (heterozygous) and one negative control (wild type) DNA specimen was included in each PCR run. To start the reactions, 12.5 µL of U-buffer was added to each labeled PCR tube and the tubes were mixed gently by mid-speed vortex before being placed on the PCR machine.

During the PCR thermal cycling procedure, the PCR tubes were subjected to a starting temperature of 95° C. for 4 minutes, followed by 5 cycles (95° C. for 30 seconds, 68° C. for 45 seconds, and 72° C. for 1 minute), followed by 25 cycles (95° C. for 30 seconds, 70° C. for 45 seconds, and 72° C. for 1 minute), followed by 7 minutes at 72° C. To melt the DNA double strands, each PCR tube was incubated at 96° C. for 2 minutes. In addition, the branched DNA formation was initiated by placing the denatured DNA at 65° C. for 30 minutes and then incubating the reaction at 4° C. for 30 minutes.

The following methods and materials were used in conjunction with the cloned Pfu polymerase. Fifteen minutes before use, the 1OX polymerase buffer, 10 mM dNTP mix, 50 mM $MgCl_2$, and a primer mix was warmed to room temperature. The primer mix was made as follows. A 100 µL solution of each primer (Dig-Primer1; Bt-Primer1; Primer2; and Primer3) was made in double distilled water to have a concentration of 12.5 µM. An equal volume of each 100 µL solution then was mixed together to make the primer mix. The final concentration of each primer in this primer mix was 3.125 µM.

The PCR reaction buffer (L-Buffer) and polymerase working solution (U-Buffer) were made in separated 250-µL Eppendorf tubes. For 10 PCR reactions each having a total volume of 50 µL, the L-Buffer and U-Buffer was made as follows:

|  | L-Buffer | U-Buffer |
| --- | --- | --- |
| Nuclease-free water | 305 µL | 112.5 µL |
| 10 X polymerase buffer | 37.5 µL | 12.5 µL |
| 50 mM $MgCl_2$ | 36 µL |  |
| Primer mix | 40 µL |  |
| 10 mM dNTP mix | 5 µL |  |
| Cloned Pfu polymerase |  | 6.5 µL |
| Total volume | 423.5 µL | 131.5 µL |

Once the ingredients were added, the tubes were mixed gently by mid-speed vortex.

To setup each PCR reaction, 37.5 µL of L-Buffer was transferred to each labeled PCR tube and the U-Buffer was maintained on ice. The labeled PCR and U-Buffer then were brought to the PCR room where 1 µL of genomic DNA (around 50 ng/µL) was added to each labeled PCR tube. The labeled PCR tubes then were mixed by mid-speed. Again, one positive control (heterozygous) and one negative control (wild type) DNA specimen was included in each PCR run. To start the reactions, 12.5 µL of U-buffer was added to each labeled PCR tube and the tubes were mixed gently by mid-speed vortex before being placed on the PCR machine. During the PCR thermal cycling procedure, the PCR tubes were subjected to a starting temperature of 95° C. for 4 minutes, followed by 5 cycles (95° C. for 30 seconds, 69° C. for 45 seconds, and 72° C. for 1 minute), followed by 25 cycles (95° C. for 30 seconds, 70° C. for 45 seconds, and 72° C. for 1 minute), followed by 7 minutes at 72° C. To melt the DNA double strands, each PCR tube was incubated at 96° C. for 2 minutes. In addition, the branched DNA formation was initiated by placing the denatured DNA at 65° C. for 30 minutes and then incubating the reaction at 4° C. for 30 minutes.

The PCR primers Dig-Primer1, Bt-Primer1, Primer2, and Primer3 as well as the two PCR protocols were designed to amplify a DNA fragment of about 400 base pairs that contained the region surrounding position 1691 of exon 10 of the Factor V gene. Analysis of the PCR products revealed that the primers and protocols amplified a 400 base pair fragment. Briefly, 2% agarose gel electrophoresis of the PCR products generated by either the native or the cloned Pfu protocol resolved a single band of DNA having 400 base pairs, confirming that each PCR protocol specifically amplifies the targeted region of exon 10 of the Factor V gene.

To detect heterozygous carriers, the PCR products were examined using a luminescence oxygen channeling immunoassay (LOCI) method as follows. Briefly, the LOCI reagents were 1X LOCI buffer (10 mM Tri-HCl, pH 8.3; 4 mM $MgCl_2$; 50 mM KCl; and 200 μg/ml nuclease-free BSA) and two types of detection beads (Behring Diagnostics). The blue detection beads were sensitizer beads coated with streptavidin (2300 streptavidin/bead at a concentration of 500 μg/ml in 1X LOCI buffer). The yellow beads were acceptor or chemiluminescent beads coated with anti-digoxigenin antibody (2.5 mg/ml in 1X LOCI buffer). Each of these LOCI reagents were stored in a black box at 4° C. To perform the LOCI reaction, 4 μL of the PCR amplification product from each PCR tube were transferred to each LOCI detection tube (a labeled 650-μL Eppendorf tube). An empty tube was included in each assay as an assay blank. The LOCI detection tubes then were brought to a dark room and a detection solution (1 mL of 1 x LOCI buffer; 5 μL of the blue beads; and 5 μL of the yellow beads) prepared and mixed by mid-speed vortex. Once prepared, 100 μL of the detection solution were transferred to each LOCI detection tube and the tubes mixed gently by low speed vortex. After mixing, the LOCI detection tubes were incubated at 37° C. for 30 minutes. After incubation, the LOCI signal was read using a LOCI machine (MPL-250; Behring). A high LOCI reading indicates that the specimen is heterozygous for Factor V Leiden, while a low LOCI reading indicates that the specimen is either homozygous for Factor V Leiden or wild-type.

Since low LOCI readings mean the sample is either homozygous for Factor V Leiden or wild-type, a mixing test was performed to detect homozygous carriers. Briefly, 10 μL of each PCR product giving a low LOCI reading was mixed with 10 μL of the PCR product from a known negative control. The known negative control contained DNA that was homozygous for wild-type Factor V. To melt all the double stranded DNA, the mixed DNA samples were heated at 96° C. for 2 minutes. After melting, the mixed DNA samples were incubated at 65° C. for 30 minutes to form branched DNA, followed by chilling at 4° C. for 30 minutes. After chilling the samples for 30 minutes, LOCI readings were taken. At this point, a high LOCI reading indicates that the specimen is homozygous for Factor V Leiden, while a low LOCI reading indicates that the specimen is wild-type for Factor V.

A signal to noise ratio (S/N) was determined to minimize variations between assays. Specifically, the S/N was obtained by dividing the LOCI reading obtained from each PCR product by the LOCI reading obtained from the assay blank. The S/N was above 10 for heterozygous carriers and below 5 for wild-type DNA when either the native or cloned Pfu Protocol was used.

Twenty (20) known heterozygous DNA specimen were tested to determine the sensitivity of detecting heterozygous DNA. For all 20 samples, high S/N results were obtained, indicating that the sensitivity for a true heterozygous carrier was 100%. In addition, 11 known wild-type specimen were tested to determine specificity. For all 11 samples, low S/N results were obtained, indicating that the specificity for a true wild-type specimen was 100%. Further, seven known homozygous DNA samples were tested by the direct assay as well as by the mixing test to determine the sensitivity of detecting homozygous DNA. For all seven sample, low S/N results were obtained for the direct assay and high S/N results obtained upon mixture with a known wild-type DNA sample, indicating that the sensitivity for a true homozygous carrier was 100%. Performing the mixing test on a known wild-type specimen resulted in a low S/N result.

Fourteen (14) specimen were tested using the native Pfu protocol in a blind fashion. The S/N results obtained then were compared with results obtained using bi-PASA, a standard assay performed in coagulation labs. Five heterozygous and nine wild-type specimen were correctly identified.

In addition, 50 specimen were tested using the cloned Pfu protocol in a blind fashion. The S/N results obtained then were compared with those from bi-PASA. Twenty-four (24) heterozygous and 26 wild-type specimen were correctly identified. It is noted that one disagreement between the LOCI method and bi-PASA method was observed. Re-evaluation using both methods, however, revealed that the original result obtained by the bi-PASA method was incorrect. Thus, the second analysis confirmed that the original result obtained using the LOCI methods described herein was correct.

In a separate analysis, a total of 137 samples were analyzed in blind fashion. Nine samples produced positive results but were negative by the bi-PASA technique (false positives). To eliminate the false positive results, additional oligonucleotide primers were designed. These primers were designed to amplify a 260 base pair fragment of nucleic acid spanning the G1691 site of Factor V, eliminating much of the intronic sequence amplified by the Dig-Primer1, Bt-Primer1, Primer2, and Primer3 primers.

In this analysis, the two upper primers were again Dig-Primer1 and Bt-Primer1. The two lower primers (Primer4 and Primer5), however, were different from Primer2 and Primer3. Specifically, Primer4 and Primer5 were designed to have an identical sequence at the 3'-end and a different sequence at the at the 5'-end of the primer. The sequence of Primer4 (SEQ ID NO:4) and Primer5 (SEQ ID NO:5) is as follows with the identical sequences being underlined:
5'-ACCATGCTCGAGATTACGAGGGTTACTTCAAGG ACAAAATA-3' (SEQ ID NO:4)
5'-GATCCTAGGCCTCACGTATTGGTTACTTCAAGGA CAAAATA-3' (SEQ ID NO:5).

The PCR reactions and LOCI detection methods were as described above with the following changes. The PCR reaction buffer (L-Buffer) and polymerase working solution (U-Buffer) were made in separated 250-μL Eppendorf tubes. For 10 PCR reactions each having a total volume of 50 μL, the L-Buffer and U-Buffer was made as follows:

|  | L-Buffer | U-Buffer |
| --- | --- | --- |
| Nuclease-free water | 316.8 μL | 130 μL |
| 10 X polymerase buffer | 40 μL | 7.9 μL |
| 50 mM $MgCl_2$ | 30 μL |  |
| Primer mix | 16.8 μL |  |
| 10 mM dNTP mix | 4.18 μL |  |
| Native Pfu polymerase |  | 6.25 μL |
| Total volume | 407.8 μL | 144.15 μL |

To setup each PCR reaction, 37.5 μL of L-Buffer was transferred to each labeled PCR tube and the U-Buffer was maintained on ice. The labeled PCR and U-Buffer then were brought to the PCR room where 1 μL of genomic DNA (around 50 ng/μL) was added to each labeled PCR tube. The labeled PCR tubes then were mixed by mid-speed. Again, one positive control (heterozygous) and one negative control (wild type) DNA specimen was included in each PCR run. To start the reactions, 12.5 μL of U-buffer was added to each labeled PCR tube and the tubes were mixed gently by mid-speed vortex before being placed on the PCR machine.

During the PCR thermal cycling procedure, the PCR tubes were subjected to a starting temperature of 95° C. for 4 minutes, followed by 5 cycles (95° C. for 30 seconds, 67° C. for 45 seconds, and 72° C. for 1 minute), followed by 27 cycles (95° C. for 30 seconds, 69° C. for 45 seconds, and 72° C. for 1 minute), followed by 7 minutes at 72° C. To melt the DNA double strands, each PCR tube was incubated at 96° C. for 2 minutes. In addition, the branched DNA formation was initiated by placing the denatured DNA at 65° C. for 30 minutes and then incubating the reaction at 4° C. for 30 minutes.

The false positive samples were analyzed using the Dig-Primer1, Bt-Primer1, Primer4, and Primer5 primers. In each case, the samples were correctly identified as either negative (−/−) or positive (+/−). These results demonstrate that the intronic sequences after exon 10 potentially contain polymorphisms since the elimination of intronic sequences avoided the false positive results.

Example 2—Factor V Leiden Detection from Whole Blood

Stable nucleic acid branching structures were detected in a cell lysate mixture containing amplified nucleic acid. The presence of stable branching structures indicates that the region amplified corresponds to a region containing heterologous alleles.

To prepare a cell lysate, 200 μL of whole blood (WB) was placed into a 0.5 mL tube and an equal volume (200 μL) of 0.14M NH$_4$CL, 0.017M Tris, pH 7.4 was added. The tube then was vortexed for 5 seconds and placed on ice for 5 minutes. After removing the tube from the ice, the tube was centrifuged at 1000 x g for 1 minute. When a fixed speed microcentrifuge was used, the tube was pulsed in 3 second intervals four times for a total pulse time of about 12 seconds.

After centrifugation, the supernatant was removed and discarded. The remaining pellet was washed three times as follows: 200 μL of 1X PCR Buffer (2 mM MgCl$_2$; 20 mM Tris (pH8); 10 mM KCl; 0.1% Triton X-100; and 6 mM (NH$_4$)$_2$SO$_4$) was added, the tube vortexed briefly and centrifuged (1000 x g for 1 minute, or when a fixed speed microcentrifuge was used, pulsed in 3 second intervals four times for a total pulse time of about 12 seconds), and the supernatant removed and discarded. Twenty (20) μL 1X TE and 20 μL GeneReleaser™ (BioVentures, Inc) were added to the remaining pellet. The tube then was vortexed for 5 seconds and microwaved for seven minutes using a microwave oven (4500 Watt-Minutes total). Following the microwave treatment, the tube was centrifuged for 30 seconds, and 20 μL of the supernatant containing the nucleic acid released from the cells was transferred to a fresh tube. A 2.5 μL aliquot of the supernatant containing the nucleic acid was used per 51 μL PCR reaction.

For each PCR reaction, the PCR reaction buffer (L-Buffer) and polymerase working solution (U-Buffer) were as follows:

|  | L-Buffer | U-Buffer |
| --- | --- | --- |
| Nuclease-free water | 31.6 μL | 12.25 μL |
| 10 X polymerase buffer | 3.75 μL | 1.25 μL |
| Primer mix | 4 μL |  |
| 10 mM dNTP mix | 0.5 μL |  |
| Native Pfu polymerase |  | 0.6 μL |
| Total volume per reaction | 36 μL | 12.5 μL |

To setup each PCR reaction, 36 μL of L-Buffer, 2.5 μL of either DNA (around 10 ng/μL) or cell lysate, and 12.5 μL of U-Buffer were combined in a PCR tube that was then placed on the PCR machine. During the PCR thermal cycling procedure, the PCR tubes were subjected to a starting temperature of 95° C. for 4 minutes, followed by 5 cycles (95° C. for 30 seconds, 60° C. for 45 seconds, and 72° C. for 1 minute), followed by 30 cycles (95° C. for 30 seconds, 65° C. for 45 seconds, and 72° C. for 1 minute), followed by 7 minutes at 72° C. Following nucleic acid amplification, additional MgCl$_2$ was added to each tube to a final concentration of 4 mM. To melt the DNA double strands, each PCR tube was incubated at 96° C. for 2 minutes. In addition, the branched DNA formation was initiated by placing the denatured DNA at 65° C. for 30 minutes and then incubating the reaction at 4° C. for 30 minutes.

The methods used to detect nucleic acid branching structures were similar to those used in Example 1.

Three of three samples containing known mutations were correctly identified (Table III). Two samples were classified as false positive, and 17 of 19 samples were correctly classified as wild-type (non-mutation). This method did not identify any false negative samples. Thus, 5 (three true positives and two false positives) of 22 samples tested (about 23%) would require mutational confirmation analysis. In a repeat experiment, one of the false positive samples were re-classified as negative. Pico Green Fluorescence, measured in relative fluorescence units (rfu's), was used to verify PCR amplification and thus prevent PCR failures from being mis-identified as wild-type.

TABLE III

Factor V analysis directly from whole blood samples

| Coag Lab Result | LOCI counts | Pico Green rfu's | Loci Results |
| --- | --- | --- | --- |
| +/− | 102991 | 7,768 | + |
| −/− | 7140 | 5,738 | − |
| +/− | 226741 | 25,986 | + |
| −/− | 5125 | 21,676 | − |
| −/− | 23713 | 14,558 | − |
| −/− | 2447 | 11,902 | − |
| −/− | 3251 | 6,776 | − |
| −/− | 5126 | 10,810 | − |
| −/− | 56177 | 11,656 | FP; repeated = neg |
| −/− | 2727 | 10,750 | − |
| −/− | 2424 | 9,438 | − |
| −/− | 1601 | 14,172 | − |
| −/− | 7651 | 9,056 | − |
| −/− | 2749 | 10,014 | − |
| −/− | 3863 | 12,894 | − |
| −/− | 3465 | 11,292 | − |
| −/− | 4163 | 6,720 | − |
| −/− | 117,483 | 10,092 | FP |
| +/− | 143385 | 11,446 | + |
| −/− | 7759 | 6,436 | − |
| −/− | 3902 | 9,964 | − |

Example 3—Cystic Fibrosis Exon 10 Mutation Detection from Whole Blood

Stable nucleic acid branching structures were detected in a cell lysate mixture containing amplified nucleic acid. The presence of stable branching structures indicates that the region amplified corresponds to a region containing heterologous alleles. For the detection of cystic fibrosis mutations, the cell lysate was prepared as described in Example 2. In addition, the PCR reactions were performed using 2 µL of cell lysate and 38 µL of a mixture containing 1X polymerase buffer, 0.4 mM dNTPs, 0.625 mM each primer, 0.0156 units/mL native Pfu polymerase, and 0.0156 units/mL exo Pfu. The PCR amplification conditions were as follows: starting temperature of 96° C. for 2 minutes, followed by 40 cycles (95° C. for 15 seconds, 60° C. for 30 seconds, and 72° C. for 45 seconds), followed by 7 minutes at 72° C. Following nucleic acid amplification, additional $MgCl_2$ was added to each tube to a final concentration of 4 mM.

The oligonucleotide primers amplified a 200 base pair region of Exon 10 of the cystic fibrosis gene. The two forward primers (Dig-Primer12 and Bt-Primer12) were designed to have the same sequence (5'-CTCAGTTTTCCTGGATTATGCC-3'; SEQ ID NO:12) with a different binding agent attached at the 5'-end: one having digoxigenin (Dig-Primer12) and the other having biotin (Bt-Primer12).

The two lower primers (Primer13 and Primer14) also target the cystic fibrosis gene. These two primers were designed to have an identical sequence at the 3'-end and a different sequence at the at the 5'-end of the primer. The sequence of Primer13 (SEQ ID NO:13) and Primer14 (SEQ ID NO:14) is as follows with the identical sequences being underlined:
5'-ACCATGCTCGAGATTACGAGCTAACCGATTGA ATATGGAGCC-3' (SEQ ID NO:13)
5'-GATCCTAGGCCTCACGTATTCTAACCGATTGAA TATGGAGCC-3' (SEQ ID NO:14)

After completion of PCR, branch migration was carried out under these conditions: denaturation at 96° C. for 2 minute and branch migration at 65° C. for 30 minutes followed by a 4° C. hold. Upon completion of branch migration, 3 µL of amplified product was mixed with 100 µL of 1X LOCI buffer (10 mM Tris-HCl, 50 mM KCl, 4 mM $MgCl_2$, 200 µg/mL BSA) containing of chemiluminescent sensitizer beads (0.25 mg/mL) and acceptor beads (0.25 mg/mL). These reactions were incubated in the dark at 37° C. for 30 minutes. The samples were illuminated, and chemiluminescence was detected using the DNA LOCI reader.

Two of two samples containing known mutations were correctly identified (Table IV). One sample was classified as a false positive, and 19 of 20 samples were classified correctly as wild-type including two heterozygous mutations in exon 4. This method did not identify any false negative samples. Thus, three (two true positives and one false positive) of 22 samples tested (about 14%) would require mutational confirmation analysis.

TABLE IV

Cystic Fibrosis gene exon 10 molecular genetics using whole blood samples

| Molecular Genetics Results | LOCI counts | Pico Green (rfu's) | LOCI Results Exon 10 |
|---|---|---|---|
| neg | 2263 | 12,296 | − |
| neg | 2613 | 9,466 | − |
| neg | 2330 | 8,196 | − |
| neg | 1990 | 8,054 | − |
| neg | 2015 | 8,968 | − |
| Hetero (Exon 4) | 2110 | 8,004 | − |
| Hetero (Exon 10) | 230041 | 9,258 | + |
| neg | 2169 | 9,304 | − |
| neg | 2856 | 13,702 | − |
| neg | 2650 | 11,624 | − |
| neg | 2082 | 7,748 | − |
| Hetero (Exon 4) | 2619 | 10,204 | −(Exon 10) |
| neg | 2772 | 9,898 | − |
| neg | 2847 | 7,420 | − |
| neg | 3259 | 8,636 | − |
| neg | 1986 | 5,698 | − |
| neg | 2525 | 9,348 | − |
| neg | 2585 | 10,304 | − |
| neg | 119352 | 7,342 | FP-confirmed to be G1716A polymorphism |
| neg | 2053 | 8,114 | − |
| Hetero (Exon 10) | 241577 | 10,364 | + |
| neg | 2371 | 10,972 | − |

Example 4—Factor V Leiden and Cystic Fibrosis Exon 10 Mutation Detection using a Sandwich Immunoassay To detect Factor V Leiden mutations using a microtiter plate format, Dig-Primer1, Bt-Primer1, Primer6, and Primer7 primers were used to amplify a 258 base pair fragment containing the Factor V Leiden site. Primer6 and Primer7 were designed to have an identical sequence at the 3'-end and a different sequence at the at the 5'-end of the primer. The sequence of Primer6 (SEQ ID NO:6) and Primer7 (SEQ ID NO:7) is as follows with the identical sequences being underlined:
5'-ACCATGCTCGAGATTACGAGTTACTTCAAGGA CAAAATACC-3' (SEQ ID NO:6)
5'-GATCCTAGGCCTCACGTATTTTACTTCAAGGAC AAAATACC-3' (SEQ ID NO:7).

The PCR reaction buffer (L-Buffer) and polymerase working solution (U-Buffer) were as follows for each PCR reaction:

|  | L-Buffer | U-Buffer |
|---|---|---|
| Nuclease-free water | 27 µL | 10 µL |
| 10 X polymerase buffer | 3.5 µL | 1.5 µL |
| Primer mix | 4 µL |  |
| 10 mM dNTP mix | 0.5 µL |  |
| Native Pfu polymerase |  | 1 µL |
| Total volume per reaction | 35 µL | 12.5 µL |

To setup each PCR reaction, 35 µL of L-Buffer, 2.5 µL of either DNA (around 10 ng/µL) or cell lysate, and 12.5 µL of U-Buffer were combined in a PCR tube that was then placed on the PCR machine. The PCR amplification conditions were as follows: 95° C. for 2 minutes, followed by 40 cycles (95° C. for 15 seconds, 64° C. for 30 seconds, and 72° C. for 1 minute), followed by a final extension for 7 minutes at 72°

C. After the PCR amplifications, additional MgCl$_2$ was added to a final concentration of 4 mM. To melt the DNA double strands, each PCR tube was incubated at 95° C. for 2 minutes. In addition, the branched DNA formation was initiated by placing the denatured DNA at 65° C. for 30 minutes and then the reaction was maintained at 4° C. until analysis.

The microtiter plate detection format was performed as follows. The amplification product from each PCR reaction was diluted 1:100 in 1X PBS, 0.1% gelatin. A 100 μL aliquot of each diluted sample then was added to a well of a streptavidin-coated plate (Boehringer Mannheim). After sealing, the plate was incubated in a 37° C. shaking incubator for one hour. After incubation, each well was washed four times with 1X PBS containing 0.05% Tween-20. Once washed, 100 μL of anti-Dig antibody conjugated with POD (horse radish peroxidase; antibody concentration of 16.67 milli units/mL in 1X PBS containing 0.05% Tween-20; Boehringer Mannheim) was added to each well, and the plate sealed and incubated in a 37° C. shaking incubator for 30 minutes. After incubation, each well was washed four times with 1X PBS containing 0.05% Tween-20, and 100 μL of diluted substrate was added to each well. The results then were read from the plate on a luminometer (Microlumat LB 96 P; EG&G Berthold).

In this analysis, 129 samples were analyzed. Based on a bi-PASA analysis, 78 samples were heterozygous for Factor V Leiden, 16 samples were homozygous for Factor V Leiden, and 35 samples were homozygous for wild-type Factor V. Using the Dig-Primer1, Bt-Primer1, Primer6, and Primer7 primers to amplify Factor V nucleic acid from whole blood and a sandwich immunoassay to detect stable branching structures, 79 samples were identified as positive for stable branching structures, 16 samples were identified as homozygous (absence of stable branching structures converted to presence of branching structures upon mixing with known homologous wild-type amplification product), and 34 samples were identified as homozygous for wild-type Factor V. The one false positive sample that was classified as homozygous for wild-type Factor V based on bi-PASA was in fact heterozygous for a mutation other than the Leiden mutation. Specifically, this sample was found to contain a G to A mutation on one allele at position 1628 based on sequencing data.

To distinguish the Factor V Leiden from this G1628A mutation or polymorphism, an additional set of primers (Primer8 and Primer9) were used with Dig-Primer1 and Bt-Primer1 to amplify a 242 base pair fragment lacking the Factor V Leiden mutation site. Primer8 and Primer9 were designed to have an identical sequence at the 3'-end and a different sequence at the at the 5'-end of the primer. The sequence of Primer8 (SEQ ID NO:8) and Primer9 (SEQ ID NO:9) is as follows with the identical sequences being underlined:
5'-ACCATGCTCGAGATTACGAGTACCTGTATTCC TCGCCTGTCCA-3' (SEQ ID NO:8)
5'-GATCCTAGGCCTCACGTATTTACCTGTATTCCT CGCCTGTCCA-3' (SEQ ID NO:9).

The amplification and detection conditions were similar to the procedures used for the Dig-Primer1, Bt-Primer1, Primer6, and Primer7 primers. In this analysis, 11 samples were analyzed. Based on a bi-PASA analysis, four samples were heterozygous for Factor V Leiden and seven samples were homozygous for wild-type Factor V. Using the Dig-Primer1, Bt-Primer1, Primer6, and Primer7 primers to amplify Factor V nucleic acid from whole blood and a sandwich immunoassay to detect stable branching structures, eight samples were identified as positive for stable branching structures and three samples were identified as homozygous for wild-type Factor V. When the Dig-Primer1, Bt-Primer1, Primer8, and Primer9 primers were used, however, four samples were identified as having heterozygous sequences and seven samples were identified as homozygous sequences. Thus, four samples are heterozygous for Factor V Leiden, four samples are heterozygous for the G1628A polymorphism, and three samples are homozygous for wild-type Factor V.

Further, two primers (Primer10 and Primer11) were designed to be used with Dig-Primer1 and Bt-Primer1 as controls. Primer10 and Primer11 have an identical sequence at the 3'-end and a different sequence at the at the 5'-end of the primer. In addition, Primer10 and Primer11 are identical to Primer8 and Primer9, respectively, with that exception of an additional two nucleotides added to their 3'-end. The sequence of Primer10 (SEQ ID NO:10) and Primer11 (SEQ ID NO: 11) is as follows with the identical sequences being underlined:
5'-ACCATGCTCGAGATTACGAGTACCTGTATTCCTC GCCTCCAGG-3'(SEQ ID NO: 10)
5'-GATCCTAGGCCTCACGTATTTACCTGTATTCCTC GCCTCCAGG-3' (SEQ ID NO: 11).

Positive results were consistently observed when the amplification and stable branching structure detection procedures were performed using the Dig-Primer1, Bt-Primer1, Primer10, and Primer11 primers.

To detect mutations in the cystic fibrosis gene using a microtiter plate format, Dig-Primer12, Bt-Primer12, Primer13 and Primer14 primers were used to amplify nucleic acid from whole blood. The amplification and detection procedures were similar to those used to detect Factor V Leiden mutations with the Dig-Primer1, Bt-Primer1, Primer6, and Primer7 primers using a microtiter plate format.

In this analysis, 111 samples were analyzed. Of the 111 samples, 38 samples were found to be heterozygous at cystic fibrosis gene exon 10 by SSCP (single stranded conformational polymorphism) analysis. All 38 of these samples also were positive for stable branching structures when the Dig-Primer12, Bt-Primer12, Primer13, and Primer14 primers were used to amplify cystic fibrosis gene exon 10 from whole blood and the sandwich immunoassay was used to detect the stable branching structures. The mean rlu's (relative light units) for these samples was 37,348. The remaining 73 samples were found not to contain polymorphisms by SSCP analysis. Of these 73 samples, only 69 samples were negative for stable branching structures upon analysis with the sandwich immunoassay method. The mean rlu's for these samples was 1,536. The four positive samples were sequenced and found to be heterologous, containing a G to A polymorphism at position 1716 (G1716A).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising four oligonucleotides, wherein said composition amplifies a region of Factor V genomic sequence during a nucleic acid amplification reaction such that amplified products that are heterologous form stable branching structures, wherein at least two of said four oligonucleotides hybridize to a Factor V genomic sequence between Factor V Leiden mutation site and the Factor V genomic sequence that hybridizes to Primer2, wherein the sequence of Primer2 is set forth in SEQ ID NO:2, and wherein said region contains the Factor V Leiden mutation site.

2. The composition of claim 1, wherein two of said four oligonucleotides are identical in nucleic acid sequence, each of said two oligonucleotides having a different label attached at the 5' end.

3. The composition of claim 2, wherein said label comprises a binding agent selected from the group consisting of biotin and digoxigenin.

4. The composition of claim 2, wherein each of said two oligonucleotides has a nucleic acid sequence as set forth in SEQ ID NO:1.

5. The composition of claim 1, wherein two of said four oligonucleotides have a 5' portion and a 3' portion, wherein said 5' portions of said two oligonucleotides are different in nucleic acid sequence, and said 3' portions of said two oligonucleotides are identical in nucleic acid sequence, and wherein said 3' portions hybridize to a sequence flanking said mutation site during said nucleic acid amplification reaction.

6. The composition of claim 5, wherein one of said two oligonucleotides has a nucleic acid sequence as set forth in SEQ ID NO:4, 5, 6, or 7.

7. The composition of claim 1, wherein said amplified products are less than about 300 bases in length.

8. The composition of claim 1, wherein at least one of said at least two oligonucleotides has a nucleic acid sequence as set forth in SEQ ID NO:4, 5, 6, or 7.

9. The composition of claim 1, wherein said four oligonucleotides are Dig-Primer1, Bt-Primer1, Primer4, and Primer5, wherein the sequence of Primer1 is set forth in SEQ ID NO:1, the sequence of Primer4 is set forth in SEQ ID NO:4, and the sequence of Primer5 is set forth in SEQ ID NO:5.

10. An oligonucleotide, wherein said oligonucleotide consists of the sequence as set forth in SEQ ID NO:1, 2, 3, 4, 5, 6, 7, 8, 9, 10, 11, 12, or 13.

11. A method of detecting heterologous Factor V alleles in an organism, said method comprising:

(a) amplifying a region of Factor V nucleic acid from said organism using oligonucleotides such that amplified products that are heterologous form stable branching structures, wherein said region contains the Factor V Leiden mutation site, and wherein at least two of said oligonucleotides hybridize to a Factor V genomic sequence between said Factor V Leiden mutation site and the Factor V genomic sequence that hybridizes to Primer2, wherein the sequence of Primer2 is set forth in SEQ ID NO:2; and (b) detecting the presence or absence of said stable branching structures, wherein the presence of said stable branching structures is indicative of the presence of said heterologous Factor V alleles in said organism.

12. The method of claim 11, wherein LOCI is used for said detecting step.

13. The method of claim 11, wherein a sandwich immunoassay is used for said detecting step.

14. A method of detecting homozygous mutant Factor V alleles in an organism, said method comprising:

(a) amplifying a region of Factor V nucleic acid from said organism using oligonucleotides to form amplification products, wherein said region contains the Factor V Leiden mutation site, and wherein at least two of said oligonucleotides hybridize to a Factor V genomic sequence between said Factor V Leiden mutation site and the Factor V genomic sequence that hybridizes to Primer2, wherein the sequence of Primer2 is set forth in SEQ ID NO:2;

(b) contacting said amplification products with a solution to form a mixture, wherein said solution comprises homozygous wild-type Factor V products amplified using said oligonucleotides; and (c) detecting the presence or absence of stable branching structures in said mixture, said stable branching structures being formed between said amplification products and said homozygous wild-type Factor V products, the presence of said stable branching structures being indicative of the presence of said homozygous mutant Factor V alleles in said organism.

15. The method of claim 14, wherein LOCI is used for said detecting step.

16. The method of claim 14, wherein a sandwich immunoassay is used for said detecting step.

* * * * *

SEQUENCE LISTING

<160> NUMBER OF SEQ ID NOS: 15

<210> SEQ ID NO 1
<211> LENGTH: 22
<212> TYPE: DNA
<213> ORGANISM: Homo sapien

<400> SEQUENCE: 1
caggcaggaa caacaccatg at                                            22

<210> SEQ ID NO 2
<211> LENGTH: 44
<212> TYPE: DNA
<213> ORGANISM: Artificial Sequence
<220> FEATURE:
<223> OTHER INFORMATION: Contains a portion of homo sapien sequence

<400> SEQUENCE: 2
accatgctcg agattacgag ttatcacact ggtgctaaaa agga                    44

<210> SEQ ID NO 3
<211> LENGTH: 44
<212> TYPE: DNA
<213> ORGANISM: Artificial Sequence
<220> FEATURE:
<223> OTHER INFORMATION: Contains a portion of homo sapien sequence

<400> SEQUENCE: 3
gatcctaggc ctcacgtatt ttatcacact ggtgctaaaa agga                    44

<210> SEQ ID NO 4
<211> LENGTH: 41
<212> TYPE: DNA
<213> ORGANISM: Artificial Sequence
<220> FEATURE:
<223> OTHER INFORMATION: Contains a portion of homo sapien sequence

<400> SEQUENCE: 4
accatgctcg agattacgag ggttacttca aggacaaaat a                       41

<210> SEQ ID NO 5
<211> LENGTH: 41
<212> TYPE: DNA
<213> ORGANISM: Artificial Sequence
<220> FEATURE:
<223> OTHER INFORMATION: Contains a portion of homo sapien sequence

<400> SEQUENCE: 5
gatcctaggc ctcacgtatt ggttacttca aggacaaaat a                       41

<210> SEQ ID NO 6
<211> LENGTH: 41
<212> TYPE: DNA
<213> ORGANISM: Artificial Sequence
<220> FEATURE:
<223> OTHER INFORMATION: Contains a portion of homo sapien sequence

<400> SEQUENCE: 6
accatgctcg agattacgag ttacttcaag gacaaaatac c                       41

<210> SEQ ID NO 7
<211> LENGTH: 41
<212> TYPE: DNA
<213> ORGANISM: Artificial Sequence
<220> FEATURE:
<223> OTHER INFORMATION: Contains a portion of homo sapien sequence

<400> SEQUENCE: 7
gatcctaggc ctcacgtatt ttacttcaag gacaaaatac c           41

<210> SEQ ID NO 8
<211> LENGTH: 43
<212> TYPE: DNA
<213> ORGANISM: Artificial Sequence
<220> FEATURE:
<223> OTHER INFORMATION: Contains a portion of homo sapien sequence

<400> SEQUENCE: 8
accatgctcg agattacgag tacctgtatt cctcgcctgt cca         43

<210> SEQ ID NO 9
<211> LENGTH: 43
<212> TYPE: DNA
<213> ORGANISM: Artificial Sequence
<220> FEATURE:
<223> OTHER INFORMATION: Contains a portion of homo sapien sequence

<400> SEQUENCE: 9
gatcctaggc ctcacgtatt tacctgtatt cctcgcctgt cca         43

<210> SEQ ID NO 10
<211> LENGTH: 43
<212> TYPE: DNA
<213> ORGANISM: Artificial Sequence
<220> FEATURE:
<223> OTHER INFORMATION: Contains a portion of homo sapien sequence

<400> SEQUENCE: 10
accatgctcg agattacgag tacctgtatt cctcgcctcc agg         43

<210> SEQ ID NO 11
<211> LENGTH: 43
<212> TYPE: DNA
<213> ORGANISM: Artificial Sequence
<220> FEATURE:
<223> OTHER INFORMATION: Contains a portion of homo sapien sequence

<400> SEQUENCE: 11
gatcctaggc ctcacgtatt tacctgtatt cctcgcctcc agg         43

<210> SEQ ID NO 12
<211> LENGTH: 22
<212> TYPE: DNA
<213> ORGANISM: Homo sapien

<400> SEQUENCE: 12
ctcagttttc ctggattatg cc                                22

<210> SEQ ID NO 13
<211> LENGTH: 42
<212> TYPE: DNA
<213> ORGANISM: Artificial Sequence
<220> FEATURE:
<223> OTHER INFORMATION: Contains a portion of homo sapien sequence

<400> SEQUENCE: 13
accatgctcg agattacgag ctaaccgatt gaatatggag cc           42

<210> SEQ ID NO 14

-continued

```
<211> LENGTH: 42
<212> TYPE: DNA
<213> ORGANISM: Artificial Sequence
<220> FEATURE:
<223> OTHER INFORMATION: Contains a portion of homo sapien sequence

<400> SEQUENCE: 14
gatcctaggc ctcacgtatt ctaaccgatt gaatatggag cc                        42

<210> SEQ ID NO 15
<211> LENGTH: 446
<212> TYPE: DNA
<213> ORGANISM: Homo sapien

<400> SEQUENCE: 15
ttatttatta tcatgaaata actttgcaaa tgaaaacaat tttgaatata ttttctttca     60
ggcaggaaca acaccatgat cagagcagtt caaccagggg aaacctatac ttataagtgg    120
aacatcttag agtttgatga acccacagaa aatgatgccc agtgcttaac aagaccatac    180
tacagtgacg tggacatcat garagacatc gcctctgggc taataggact acttctaatc    240
tgtaagagca gatccctgga caggcragga atacaggtat tttgtccttg aagtaacctt    300
tcagaaattc tgagaatttc ttctggctag aacatgttag gtctcctggc taaataatgg    360
ggcatttcct tcaagagaac agtaattgtc aagtagtcct ttttagcacc agtgtgataa    420
catttattct tttttttttt ttgtct                                         446
```